United States Patent
Cazzini et al.

(10) Patent No.: US 8,226,586 B2
(45) Date of Patent: *Jul. 24, 2012

(54) NEGATIVE PRESSURE, COMPRESSION THERAPY DEVICE

(75) Inventors: Karl Cazzini, Orchard Park, NY (US); Thomas P. Stewart, Orchard Park, NY (US)

(73) Assignee: Stryker Corporation, Kalamazoo, MI (US)

( * ) Notice: Subject to any disclaimer, the term of this patent is extended or adjusted under 35 U.S.C. 154(b) by 403 days.

This patent is subject to a terminal disclaimer.

(21) Appl. No.: 11/709,587

(22) Filed: Feb. 22, 2007

(65) Prior Publication Data

US 2008/0208088 A1    Aug. 28, 2008

(51) Int. Cl.
*A61F 5/00* (2006.01)
*A61F 7/00* (2006.01)
*A61H 7/00* (2006.01)
*A61H 1/00* (2006.01)

(52) U.S. Cl. ............. 602/13; 607/104; 607/111; 601/6; 601/9; 601/27

(58) Field of Classification Search ............. 602/13, 602/3, 4; 601/151, 27, 6, 9, 10, 33, 34, 152; 128/DIG. 20; 607/96, 104, 108, 111
See application file for complete search history.

(56) References Cited

U.S. PATENT DOCUMENTS

| | | | | |
|---|---|---|---|---|
| 4,772,259 A | * | 9/1988 | Frech et al. | 604/23 |
| 5,489,259 A | * | 2/1996 | Jacobs et al. | 602/13 |
| 5,868,690 A | * | 2/1999 | Eischen, Sr. | 601/151 |
| 6,589,194 B1 | * | 7/2003 | Calderon et al. | 601/151 |
| 6,689,079 B2 | * | 2/2004 | Flick et al. | 602/13 |
| 6,945,944 B2 | * | 9/2005 | Kuiper et al. | 602/13 |
| 6,974,442 B2 | * | 12/2005 | Grahn et al. | 604/104 |
| 7,972,287 B2 | | 7/2011 | Stewart et al. | |
| 2008/0249593 A1 | | 10/2008 | Cazzini et al. | |
| 2010/0106230 A1 | | 4/2010 | Buchanan et al. | |

OTHER PUBLICATIONS

Office Action dated Mar. 11, 2011 for U.S. Appl. No. 11/784,057.
Notice of Allowance for U.S. Appl. No. 12/260,293.

* cited by examiner

*Primary Examiner* — Patricia Bianco
*Assistant Examiner* — Ophelia Hawthorne
(74) *Attorney, Agent, or Firm* — Warner Norcross & Judd LLP

(57) ABSTRACT

A negative pressure, compression therapy device is described in this application. It has (a) a heel care boot having a fluid, (b) a pressure bag having an opening that receives the patient's foot and the heel care boot, and (c) a vacuum system that generates a modulatable negative pressure in the pressure bag. The negative pressure in the pressure bag is sufficient to cause the patient's veins to vasodilate and the negative pressure modulates to cause the fluid in the heel care boot to provide compression therapy to the patient.

12 Claims, 4 Drawing Sheets

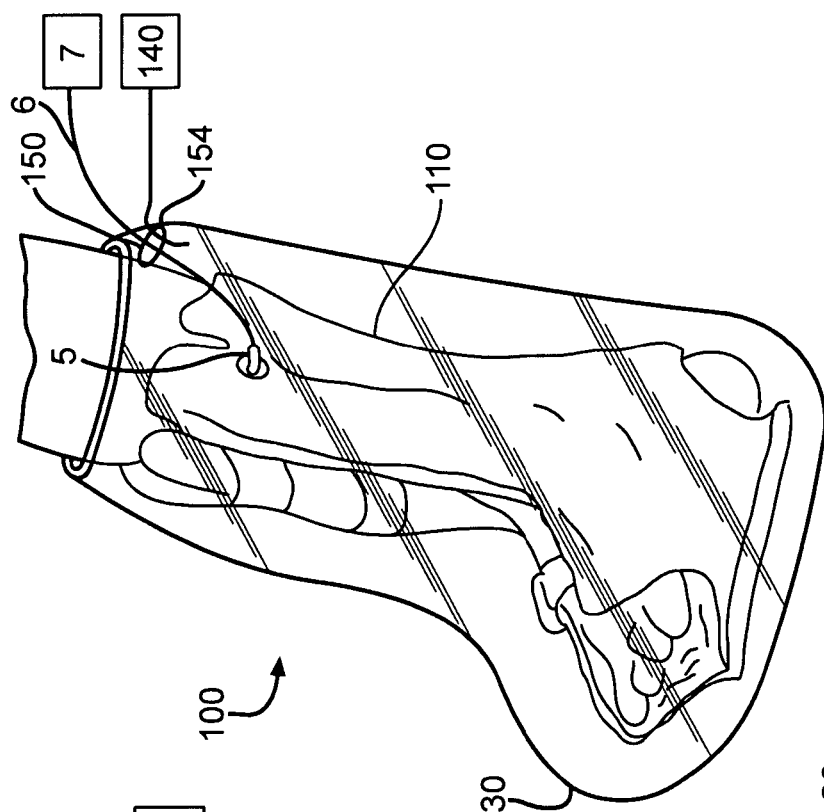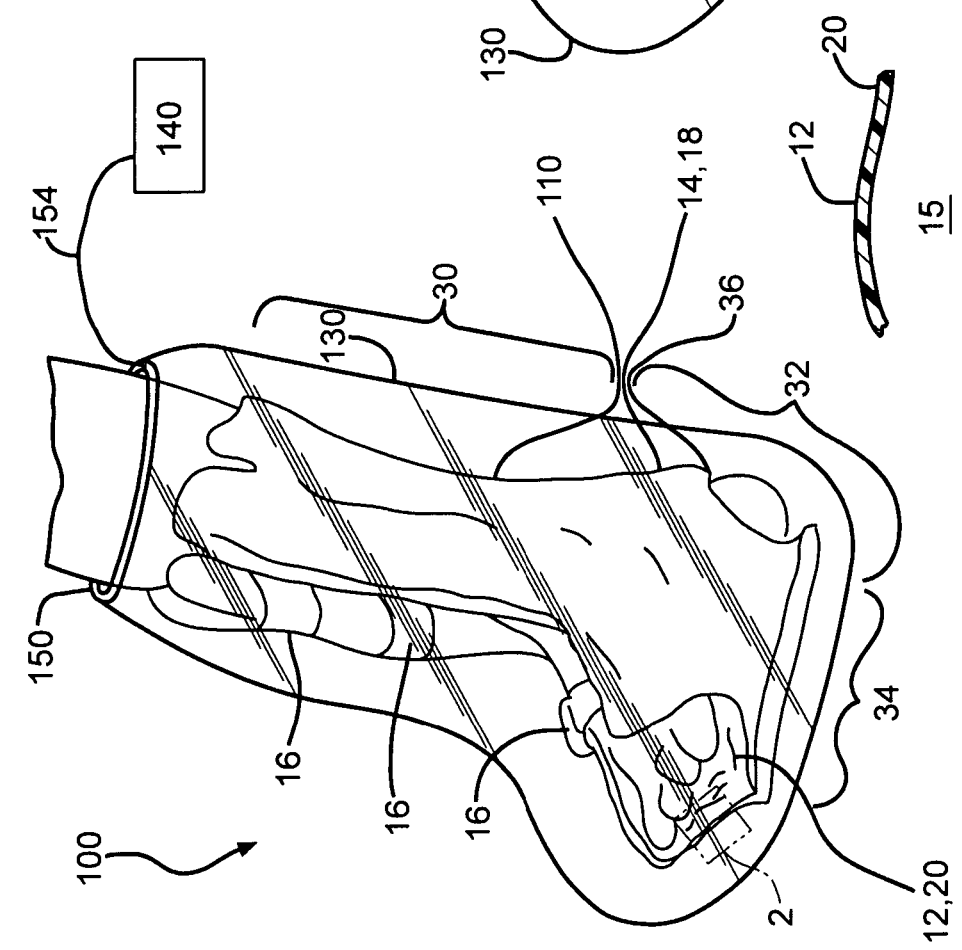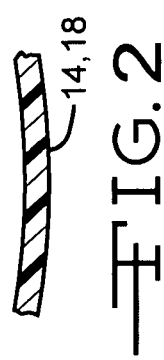

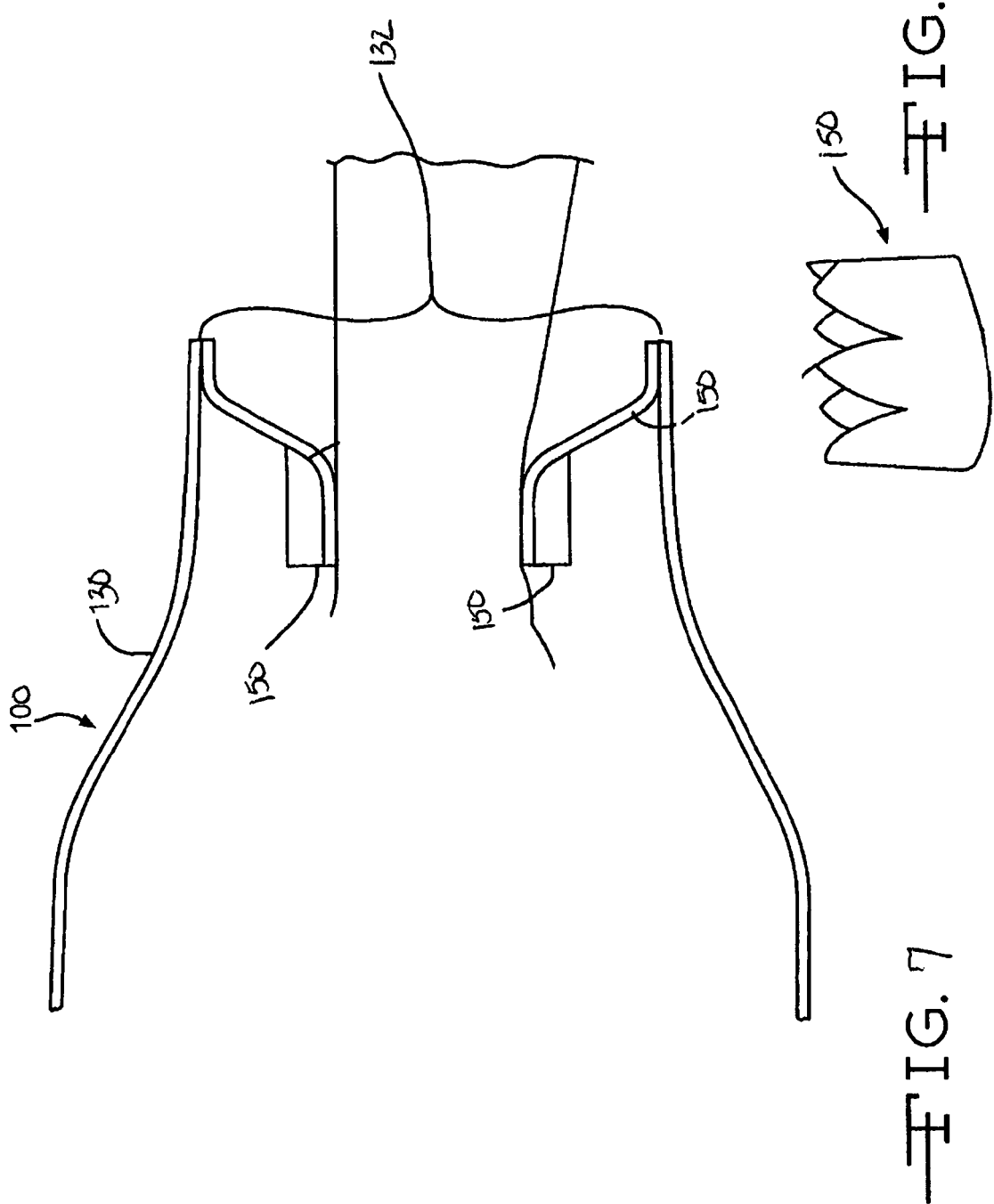

NEGATIVE PRESSURE, COMPRESSION THERAPY DEVICE

FIELD OF THE INVENTION

The present invention is directed to an alternative embodiment of applying negative pressure and compression therapy to a patient.

BACKGROUND OF THE INVENTION

Gaymar Industries, Inc. manufactures a Sof•Care Heel-Care boot. It has been manufacturing that pre-inflated heel care boot since 1982. A description of that pre-inflated heel care boot, identified only as item 110, is illustrated in FIGS. 1 and 5 and described in the detailed description of the invention.

Another heel boot embodiment is illustrated and described in U.S. Pat. No. 5,489,259 to Jacobs et al. The heel care boot described and illustrated by Jacobs et al. is extremely similar to Gaymar's Sof•Care HeelCare boot except it has a valve to receive a conduit. That conduit directs a fluid from a pressurized fluid source into the heel boot.

In U.S. Pat. No. 6,945,944, Kuiper et al. discloses "a therapeutic limb covering and an associated method of treating chronic swelling of a limb. The limb covering is uses hydrostatic pressure provided by liquid contained within the covering to apply pressure to the limb. The limb covering comprises a substantially non-distensible flexible outer layer, a distensible flexible inner layer joined together and a liquid tight bladder therebetween. The covering may be adapted for releasable securement about a limb such as an arm or a lower leg and foot of a patient. After placement on the limb, when the bladder is filled with a liquid, such as water, it expands to contact and apply pressure to the limb." The liquid can be drawn into the boot by a vacuum through a syringe.

SUMMARY OF THE INVENTION

A negative pressure, compression therapy device is described in this application. It has (a) a heel care boot having a fluid, (b) a pressure bag having an opening that receives the patient's foot and the heel care boot, and (c) a vacuum system that generates a modulatable negative pressure in the pressure bag. The negative pressure in the pressure bag is sufficient to cause the patient's veins to vasodilate and the negative pressure modulates to cause the fluid in the heel care boot to provide compression therapy to the patient.

BRIEF DESCRIPTION OF THE FIGURES

FIG. 1 illustrates an embodiment of a negative pressure, compression therapy device.

FIG. 2 illustrates a cross-sectional view of FIG. 1 taken from box 2.

FIGS. 3 to 5 illustrate alternative embodiments of FIG. 1.

FIGS. 7 and 8 illustrate another alternative soft seal embodiment—FIG. 7 illustrates the soft seal in the bag and FIG. 8 illustrates the soft seal in the crown formation.

DETAILED DESCRIPTION OF THE INVENTION

Figure 5:
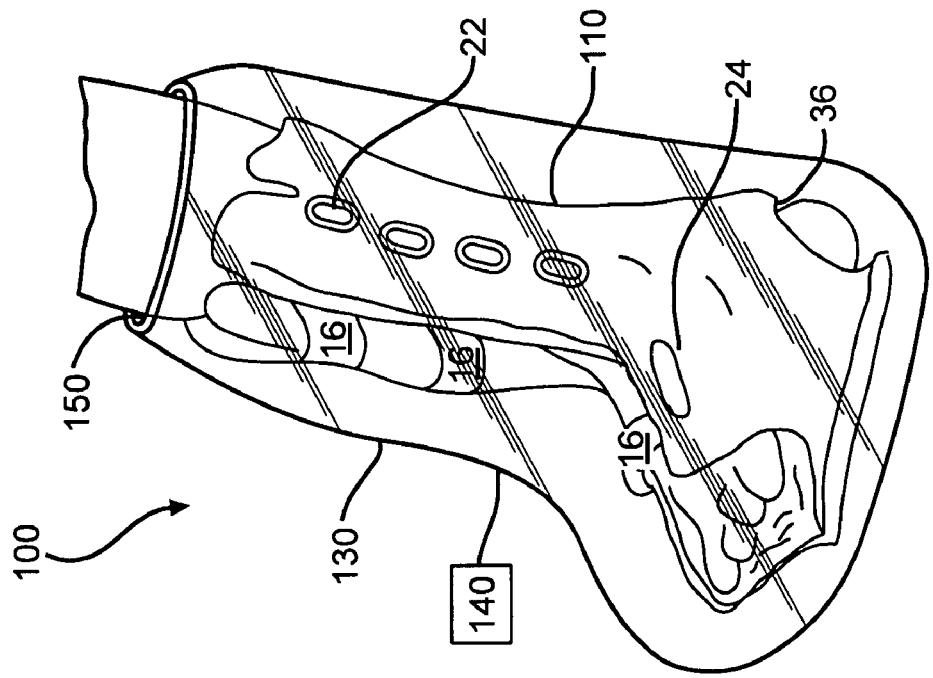

As illustrated in FIG. 1, a disposable negative pressure, compression therapy device 100 has (1) a heel care boot 110, (2) a disposable pressure bag 130 that can enclose the heel care boot 110 (3) a vacuum system 140 that generates a modulatable negative pressure in the disposable pressure bag 130, and (4) a soft seal 150 positioned at the disposable pressure bag's opening to maintain the pressure in the bag 130 and simultaneously allow the negative pressure to leak at a controlled manner and does not create a tourniquet effect, over time, as with a hard seal.

Heel Care Boot

One embodiment of a conventional heel care boot 110 is Gaymar Industries, Inc.'s Sof•Care HeelCare boot which is pre-inflated to a predetermined pressure. Other heel care boots 110 can have a valve 5 (see FIG. 3) that allows the boot to be inflated with a fluid while positioned on the foot through the fluid that passes through a conduit 6 from a pressurized fluid source 7. It is known that heel care boots are a protective device intended to receive therein and partially enclose in a cradling fashion a human's foot, heel and/or calf area, as illustrated in FIGS. 1, 3, 4, and 5. The boot conforms to the contour of the limb to normalize the interface pressure between the boot and the surface of the limb to protect the limb and to maintain a proper blood supply to the soft tissues thereof. In addition, the boot decreases the formation of and facilitates the healing of pressure sores and other types of medical pathologies.

Figure 4:
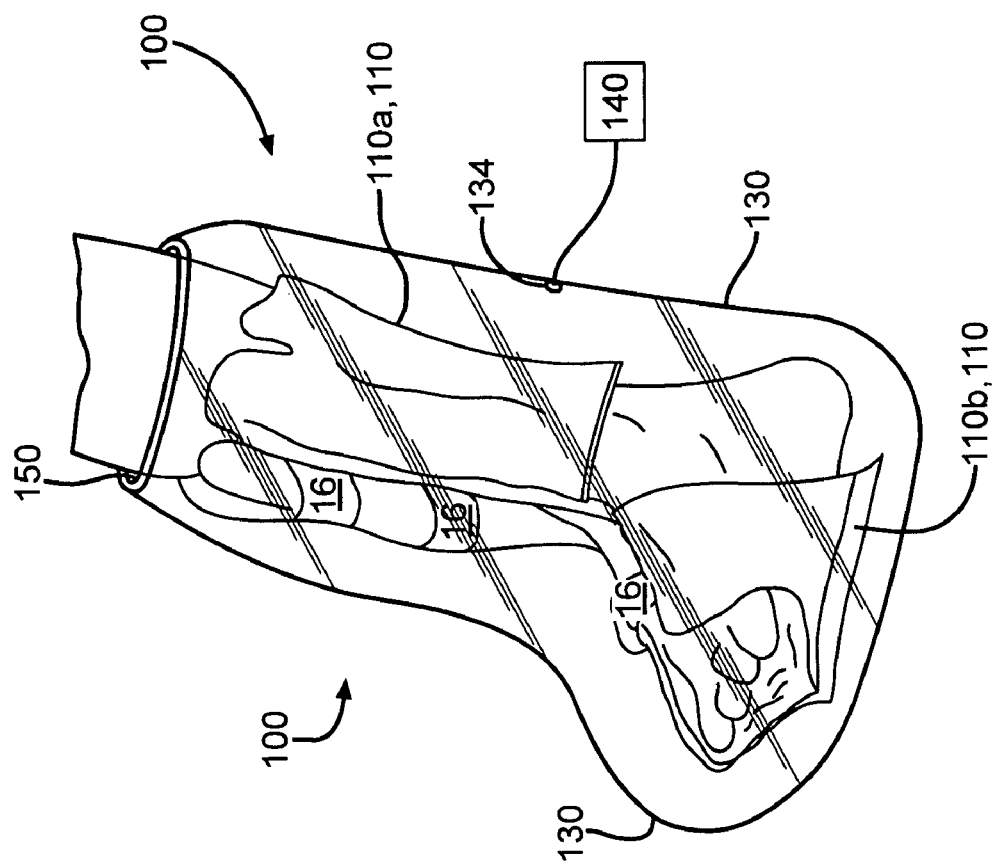

The boot 110 can be divided into distinct sections 110*a*, 110*b* as illustrated in FIG. 4. Even when divided the boot 110*a*, 110*b* operates in the same way to obtain the same result as the whole boot illustrated in FIGS. 1, 3, and 5. The embodiment illustrated in FIG. 4 can also have a valve system as illustrated in FIG. 3.

The boot has an interior surface 12 and an exterior surface 14 forming a fluid pressure chamber 15 (see FIG. 2) and fastening devices 16 for securing the boot 10 about the lower limb. Examples of fastening devices include straps and/or hook-and-loop type fasteners.

The conventional boot can have a pair of sheets, an exterior or outwardly facing sheet 18 and an interior or inwardly facing sheet 20 joined peripherally together forming the single air chamber there between. Interior and exterior sheets 18 and 20 are preferably constructed of plastic material (for example polymeric nonwoven material) and have substantially identical configurations and are adjoined at their peripheries by conventional plastic welding methods.

As illustrated in FIGS. 1, 3, and 5, the boot 110 is designated into three portions: (a) an upper portion 30 for engaging and partially enclosing a portion of the calf region of the lower limb, (b) an intermediate portion 32 for engaging and partially enclosing the ankle and Achilles tendon region of the lower limb, and (c) a lower portion 34 for engaging and partially enclosing the foot region of the lower limb.

Intermediate portion 32 can include a cut-out portion 36 integrally formed therein for receiving therein the heel of the foot. Cut-out portion 36 allows for total suspension of the heel thereby creating zero pressure, shear, heat, moisture and bacterial effects on the heel area. This is vitally important because the heel area is a primary area of ulcer formation and treatment, particularly for elderly patients.

The boot can include apertures for preventing bacterial growth, for providing visibility of the body extremity and for providing cooling. Preferably the apertures are located in the conventional boot and formed at the closure. Sheets 18, 20 can, for example, have a plurality of aligned apertures such as holes 22 (see FIG. 5) extending there through with the sheets 18, 20 being joined together by heat sealing means about the circumference of each hole 22 in an airtight fashion. The boot can further include one or more additional ventilation openings such as a slot 24 to provide ventilation to the Achilles region of the limb when the conventional boot is secured thereabout. Openings 22 and 24 act to dissipate heat and/or coolness; and moisture and provide air flow (and pressure) there through, allow palpation of the lower limb for edema (swelling), allows palpation and auscultation of the posterior tibial artery pulse, and provides visibility allowing a care giver to generally view the lower limb there through. By providing ventilation, these openings assist in keeping the lower limb substantially dry and eliminate problems normally associated with the maceration of skin and soft tissue due to continuous high moisture and heat levels, as well as prevent bacterial growth associated with moisture and heat build-up in unventilated areas.

The boot is an inexpensive product to treat pressure sores. For that reason, the boot is used in association with a single patient and then disposed. Single patient use is desirable because it decreases the chances of contaminating a patient.

Pressure Bag

The pressure bag 130, which can be disposable, is any material that can (a) surround the heel care boot 110 (110a,b) and a portion of the patient's leg and foot; and (b) contain the modulatable negative pressure generated from the vacuum system 140. An example of the material is a polymeric bag having an opening 132 to receive the patient's leg and the heel care device 110.

The pressure bag 130 may also have an aperture(s) 134 to receive a conduit(s) from the vacuum system 140 as illustrated in FIGS. 4 and 5, or the conduit 6 from the pressurized fluid source.

Soft Seal

Figure 6:
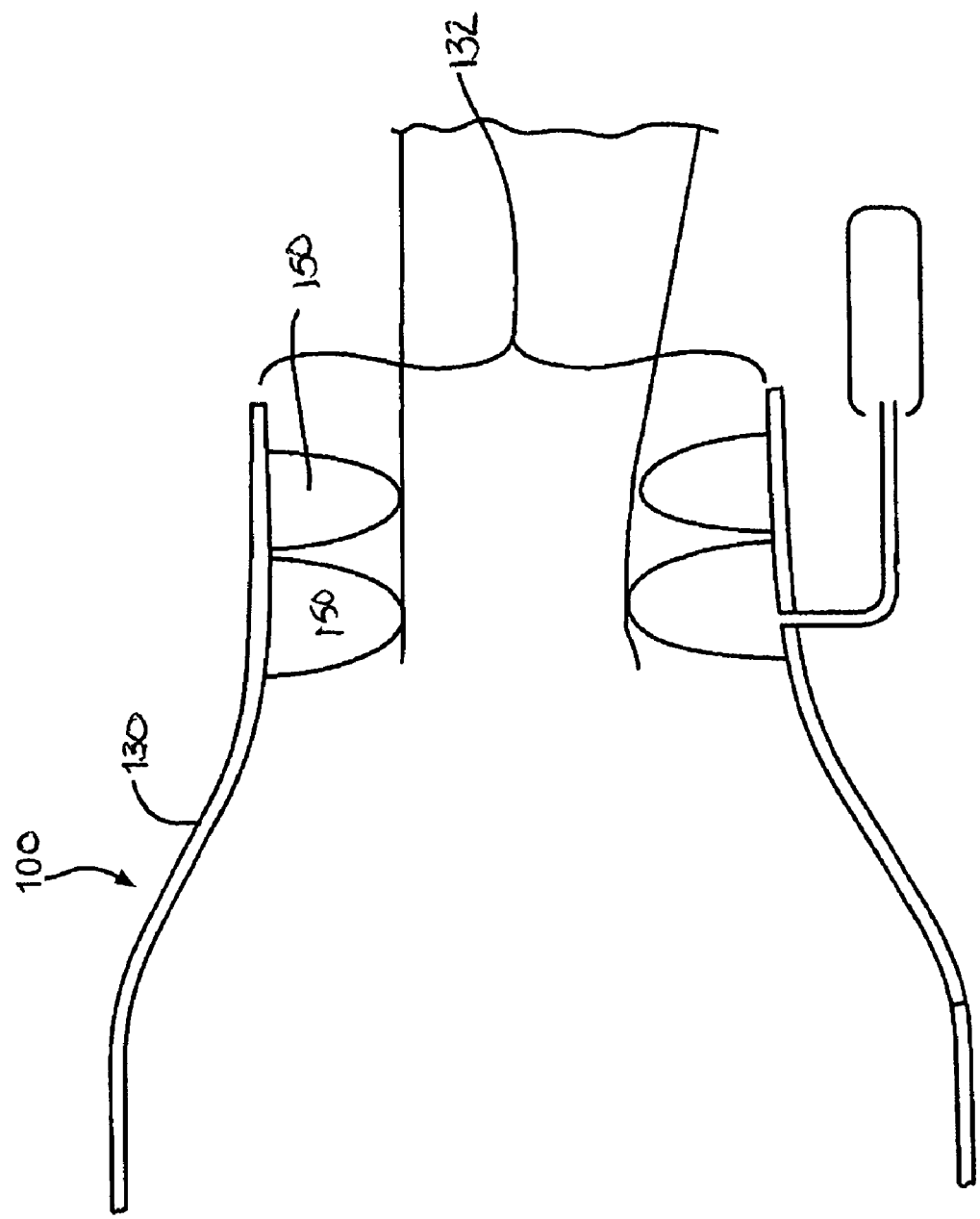
FIG. 6 illustrates an alternative soft seal embodiment.

The soft seal 150 is positioned at the opening 132 of the disposable pressure bag 130. The soft seal 150 can be an adhesive, an adhesive sheet, a plurality of adhesive sheets, an inflatable fluid bladder that expands and contracts depending on the amount of fluid that enters the bladder (see FIG. 6), and a polymeric webbing material having a crown shaped foam material positioned between the polymeric webbing material and the patient's body (see FIGS. 7 and 8). The soft seal 150 allows some of the pressure to escape and simultaneously allows the pressure to be applied to the patient's leg.

The soft seal 150 may also have an aperture 154 to receive a conduit from the vacuum system 140 as illustrated in FIG. 1 and/or the conduit 6 from the pressurized fluid source as illustrated in FIG. 3.

Vacuum System

In a preferred embodiment, the vacuum system 140 modulates the negative pressure contained within the disposable pressure bag 130. An alternative embodiment is that the vacuum system 140 generates a predetermined and constant negative pressure in the enclosure 130 that can be turned on and off.

By modulating the pressure within disposable pressure bag 130, the vacuum system's pressure causes compression therapy to be provided by the heel care boot 110. When the negative pressure within the disposable pressure bag 130 increases the negative pressure contracts the fluid contained within the heel care boot 110. And when the negative pressure within the disposable pressure bag 130 decreases the negative pressure expands the fluid contained within the heel care boot 110. The resulting expansion and contraction of the fluid within the heel care boot 110 causes the desired compression therapy.

In addition the application of a modulated negative pressure will also inhibit the build up of excessive moisture resulting from local perspiration. It is known that if the excessive moisture on the patient's body is not removed, then excessive moisture can increase the risk of pressure ulcer formation and/or ulcerous wound propagation on the patient. The modulated negative pressure, however, draws the excessive moisture away from the patient's body. By decreasing the amount of excessive moisture, the current invention further mitigates the risk of pressure ulcer formation and/or ulcerous wound propagation.

While the present invention has been described and illustrated in conjunction with a number of specific embodiments, those skilled in the art will appreciate that variations and modifications may be made without departing from the principles of the invention as herein illustrated, described and claimed. The present invention may be embodied in other specific forms without departing from its spirit or essential characteristics. The described embodiments are to be considered in all respects as only illustrative, and not restrictive. The scope of the invention is, therefore, indicated by the appended claims, rather than by the foregoing description. All changes which come within the meaning and range of equivalency of the claims are to be embraced within their scope.

We claim:

1. A negative pressure, compression therapy device comprising:
    A) a heel care boot having
        (i) an inflatable member forming a pressure chamber and within the pressure chamber is a fluid, the inflatable member having an exterior surface, an interior surface, and a portion of the interior surface contacts a part of the patient's leg, foot and/or ankle; and
        (ii) a fastening device for releasably securing the heel care boot to the patient; and
        (iii) a valve that receives a conduit that directs the fluid from a pressurized source to the pressure chamber while positioned on the patient's body to alter the positive pressure applied to the patient's foot, the heel care boot adapted to decrease the formation of and facilitate the healing of pressure sores;
    B) a pressure bag having an opening that receives the patient's foot and the heel care boot;
    C) a vacuum system generates a modulatable negative pressure in the pressure bag, the negative pressure in the pressure bag is sufficient to cause the patient's veins to vasodilate and the negative pressure modulates to cause the fluid in the heel care boot to (a) expand when the negative pressure is decreased and (b) contract when the negative pressure is increased which causes the heel care boot to provide compression therapy to the patient;
    D) a soft seal positioned at the disposable pressure bag's opening to maintain the pressure in the bag.

2. The device of claim 1 wherein the fluid in the pressure chamber is air.

3. The device of claim 1 wherein the fluid in the pressure chamber is water.

4. The device of claim 1 wherein the heel boot is disposable.

5. The device of claim 1 wherein the pressure bag is disposable.

6. The device of claim 1 wherein the inflatable member has an upper portion for at least partially enclosing a patient's leg above the ankle, an intermediate portion for at least partially enclosing the patient's ankle and heel area, and a lower portion for at least partially enclosing the patient's venous plexus area on the foot.

7. The device of claim 1 wherein the soft seal is selected from the group consisting of a first sheet and a second sheet interconnected to each other with openings therein; and a polymeric webbing material having a crown shaped foam material positioned between the polymeric webbing material and the patient's body.

8. A disposable negative pressure, compression therapy device comprising:
- A) a heel care boot having
  - (i) an inflatable member forming a pressure chamber and within the pressure chamber is a fluid, the inflatable member having an exterior surface and an interior surface that partially encloses a patient's leg above the ankle and below the knee;
  - (ii) a fastening device for releasably securing the inflatable member to the patient; and
  - (iii) a valve that receives a conduit that directs the fluid from a pressurized source to the pressure chamber while positioned on the patient's body, the heel care boot adapted to maintain a desired interface pressure between the heel care boot and the patient and to decrease the formation of and facilitate the healing of pressure sores;
- B) a disposable pressure bag having an opening that receives the patient's foot and the heel care boot;
- C) a vacuum system generates a modulatable negative pressure in the disposable pressure bag, the negative pressure in the disposable pressure bag is sufficient to cause the patient's veins to vasodilate and the negative pressure modulates to cause the fluid in the heel care boot to (a) expand when the negative pressure is decreased and (b) contract when the negative pressure is increased which causes the heel care boot to provide compression therapy to the patient; and
- D) a soft seal positioned at the disposable pressure bag's opening to maintain the pressure in the bag.

9. The device of claim 8 wherein the fluid in the pressure chamber is air.

10. The device of claim 8 wherein the fluid in the pressure chamber is water.

11. The device of claim 8 wherein the inflatable member has an upper portion for at least partially enclosing a patient's leg above the ankle, an intermediate portion for at least partially enclosing the patient's ankle and heel area, and a lower portion for at least partially enclosing the patient's venous plexus area on the foot.

12. The device of claim 8 wherein the soft seal is selected from the group consisting of an inflatable bladder positioned at or near the enclosure's opening; a first sheet and a second sheet interconnected to each other with openings therein; and a polymeric webbing material having a crown shaped foam material positioned between the polymeric webbing material and the patient's body.

* * * * *